(12) United States Patent
Coulette et al.

(10) Patent No.: US 10,161,917 B2
(45) Date of Patent: Dec. 25, 2018

(54) METHOD AND DEVICE FOR ULTRASOUND INSPECTION OF WELDS, PARTICULARLY WELDS OF BLADES ON THE DISK OF A BLADED DISK

(71) Applicant: SAFRAN AIRCRAFT ENGINES, Paris (FR)

(72) Inventors: Richard Michael Coulette, Gentilly (FR); Laurent Le Ber, Paris (FR); Pascal Jean-Christian Claude Ravault, Bry sur Marne (FR); Marc Jacky Vassault, Evry (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 205 days.

(21) Appl. No.: 14/693,966

(22) Filed: Apr. 23, 2015

(65) Prior Publication Data
US 2015/0308984 A1  Oct. 29, 2015

(30) Foreign Application Priority Data

Apr. 25, 2014  (FR) ...................................... 14 53744

(51) Int. Cl.
*G01N 29/265* (2006.01)
*G01N 29/04* (2006.01)
(Continued)

(52) U.S. Cl.
CPC ......... *G01N 29/265* (2013.01); *G01N 29/043* (2013.01); *G01N 29/223* (2013.01);
(Continued)

(58) Field of Classification Search
CPC .... G01N 29/043; G01N 29/223; G01N 29/24; G01N 29/26; G01N 29/262;
(Continued)

(56) References Cited

U.S. PATENT DOCUMENTS

| 5,513,532 A | 5/1996 | Beffy et al. |
| 6,202,489 B1 | 3/2001 | Beffy et al. |

(Continued)

FOREIGN PATENT DOCUMENTS

| EP | 2 664 915 A2 | 11/2013 |
| FR | 2 698 170 A1 | 5/1994 |

(Continued)

OTHER PUBLICATIONS

French Preliminary Search report dated Jan. 22, 2015 in French Application 14 53744, filed on Apr. 25, 2014 ( with English Translation of Categories of Cited Documents).

(Continued)

*Primary Examiner* — Natalie Huls
*Assistant Examiner* — Monica S Young
(74) *Attorney, Agent, or Firm* — Oblon, McClelland, Maier & Neustadt, L.L.P.

(57) ABSTRACT

A method and device for ultrasound testing of welds is provided. For testing element welds on a body forming a single-piece assembly with these elements, the free end of a poly-articulated robot is fitted with an ultrasound probe which is fitted with an ultrasonic multi-element array transducer; the probe is inserted into the space between two adjacent elements of the assembly; the probe is moved along three-dimensional trajectories along the profile of the element; sectorial electronic scanning is performed in at least two non-parallel testing planes; and ultrasound signals output by the transducer in order to test the welds are processed. The method and device may be applied to welds of blades on the blisk of a bladed disk.

11 Claims, 3 Drawing Sheets

(51) Int. Cl.
*G01N 29/24* (2006.01)
*G01N 29/22* (2006.01)
*G01N 29/26* (2006.01)
*G01N 29/44* (2006.01)

(52) U.S. Cl.
CPC ............. *G01N 29/24* (2013.01); *G01N 29/26* (2013.01); *G01N 29/262* (2013.01); *G01N 29/4436* (2013.01); *G01N 2291/0422* (2013.01); *G01N 2291/056* (2013.01); *G01N 2291/106* (2013.01); *G01N 2291/267* (2013.01); *G01N 2291/2693* (2013.01); *Y10S 901/44* (2013.01)

(58) Field of Classification Search
CPC ......... G01N 29/4436; G01N 2291/056; G01N 2291/267; G01N 2291/2693; G01N 29/265; G01N 2291/0422; G01N 2291/106; Y10S 901/44
See application file for complete search history.

(56) References Cited

U.S. PATENT DOCUMENTS

| | | | | |
|---|---|---|---|---|
| 6,719,184 B2* | 4/2004 | Ishida | ................ | B23K 20/1245 228/102 |
| 6,886,407 B1 | 5/2005 | Fredenberg | | |
| 7,516,022 B2* | 4/2009 | Lee | ................ | B23K 11/24 702/187 |
| 7,966,860 B2* | 6/2011 | Dijkstra | ................ | G01N 29/225 73/1.82 |
| 8,365,584 B1* | 2/2013 | Quinones | ................ | G01N 29/225 73/112.05 |
| 8,438,929 B2* | 5/2013 | Metala | ................ | G01M 13/00 73/593 |
| 8,525,831 B2* | 9/2013 | Zhang | ................ | G01N 29/0654 345/419 |
| 9,027,404 B2* | 5/2015 | Singh | ................ | G01N 29/043 73/602 |
| 2003/0079545 A1* | 5/2003 | Matney | ................ | G01N 29/11 73/627 |
| 2004/0079156 A1* | 4/2004 | Arndt | ................ | B23K 11/12 73/588 |
| 2005/0126291 A1 | 6/2005 | Czerw et al. | | |
| 2006/0219011 A1* | 10/2006 | Siddu | ................ | G01N 29/0645 73/597 |
| 2006/0230605 A1* | 10/2006 | Schlote-Holubek | ................ | B06B 1/0607 29/609.1 |
| 2006/0283250 A1 | 12/2006 | Fair et al. | | |
| 2007/0144262 A1 | 6/2007 | Aznar et al. | | |
| 2008/0149687 A1* | 6/2008 | Garnett | ................ | B23K 31/12 228/104 |
| 2008/0210009 A1* | 9/2008 | Tanishiki | ................ | G01N 29/043 73/588 |
| 2009/0078742 A1 | 3/2009 | Pasquali et al. | | |
| 2009/0165317 A1 | 7/2009 | Little | | |
| 2013/0308419 A1* | 11/2013 | Singh | ................ | G01N 29/043 367/7 |
| 2014/0238136 A1* | 8/2014 | Ten Grotenhuis | ................ | G01N 29/0654 73/592 |
| 2016/0237804 A1* | 8/2016 | Papadimitriou | .... | E21B 47/0006 |

FOREIGN PATENT DOCUMENTS

| | | |
|---|---|---|
| FR | 2 778 462 A1 | 11/1999 |
| FR | 2 883 640 A1 | 9/2006 |
| FR | 2 888 327 A1 | 1/2007 |
| JP | 8-110332 | 4/1996 |
| KR | 10-2007-0013007 A | 1/2007 |

OTHER PUBLICATIONS

Search Report dated Sep. 7, 2015 in United Kingdom Patent Application No. GB 1507004.8.

* cited by examiner

METHOD AND DEVICE FOR ULTRASOUND INSPECTION OF WELDS, PARTICULARLY WELDS OF BLADES ON THE DISK OF A BLADED DISK

TECHNICAL FIELD

This invention relates to a method and a device for ultrasound testing of welds.

It is applicable particularly for testing of blades on the disk of a bladed disk or blisk.

STATE OF PRIOR ART

Methods and devices for ultrasonic testing are already known making use of multi-element array ultrasonic transducers, as disclosed in the following documents:

FR 2 698 170, "Procédé et dispositif de contrôle ultrasonore industriel de pièces par retournement temporel", Société Nationale d'Etude et de Construction de Moteurs d'Aviation SNECMA, FR 2 778 462, <<Procédé de contrôle ultrasonore en immersion de pièces à géométrie cylindrique>>, Société Nationale d'Etude et de Construction de Moteurs d'Aviation SNECMA.

At the present time, the blades of a blisk are machined from a single-piece. It is envisaged that this machining should be replaced by friction welding, for example linear welding or as a variant by orbital friction (single orbital or multi-orbital) of blades or radial elements on the disk part or the hub, for example of a blisk for a turbomachine.

The blades and the disk part can then be machined separately, which can save an enormous amount of material since this material is lost during machining from a single piece.

Another possibility is the replacement of blades following damage during fabrication or in service.

The friction welding method may lead to surface and internal anomalies at the joint plane of the blades on the disk part. For example, it must be possible to detect them by testing in order to guarantee that the blisk is conforming. This joint plane is located in the close neighbourhood of the external periphery of the disk part or possibly in the connection filet with the flow stream, which makes it very difficult to access the zone to be tested. Furthermore, the profile of this zone to be tested is very complex and the thickness to be tested varies, which is why the three-dimensional aspect has to be taken into account for testing.

PRESENTATION OF THE INVENTION

This invention is aimed at solving this problem of testing the zone of the weld joint plane.

It uses ultrasonic testing of welds making use of a poly-articulated robot provided with an ultrasonic multi-element array transducer.

Furthermore, multi-plane electronic scanning is used to compensate for the deviation of the ultrasound beam.

Specifically, the purpose of this invention is a method for testing element welds on a body, the body and the elements that are welded to it forming a single-piece assembly, characterised in that it comprises the following steps:

equip the free end of a poly-articulated robot with an ultrasound probe, fitted with an ultrasonic multi-element array transducer;

insert the ultrasound probe into the space between two adjacent elements of the single-piece assembly facing the welded joint, corresponding to one of the two elements for which the weld is to be tested;

move the ultrasound probe along three-dimensional trajectories along the profile of the element for which the weld is to be tested;

perform a sectorial electronic scanning in at least two non-parallel testing planes, preferably approximately orthogonal; and process the ultrasound signals output by the transducer in order to test the welds.

According to one preferred embodiment of the method according to the invention, the test is a test by transverse ultrasound waves.

Preferably, testing is made by working firstly in full-skip and secondly in half-skip.

According to one preferred embodiment of the invention, the welded joint of each element is tested by performing a first pass to test the welded joint in half-skip and a second pass to test the welded joint in full-skip.

Preferably, the poly-articulated robot is used to follow the profile along each element at a first constant distance from the corresponding joint plane and at a second constant distance from it different from the first distance.

The ultrasound probe is advantageously a bevelled probe, adapted to the space between the adjacent elements of the single piece assembly.

The following test method can be used in this invention:
use a data acquisition software,
enter characteristics of the transducer, characteristics of the blisk and a test configuration in the acquisition software,
calculate delay laws for the transducer,
make a calibration on a reference part,
adjust intervals of numeric values of test parameters,
define a test sequence, and
acquire signals output by the transducer and analyse them to test the welds.

According to one particular embodiment of the invention, the elements are composed of the blades and the body consists of the disk part, of an assembly forming a turbomachine blisk, the test thus being a test of the welds of the blades on the disk part of the blisk.

Preferably, the elements of the ultrasonic multi-element array transducer are elements in a checkerboard layout.

This invention also relates to a device for testing welds of elements on a body, the body and the elements welded to it forming a single-piece assembly, characterised in that it comprises:

a poly-articulated robot capable of making three-dimensional trajectories, an ultrasound probe, fitted with an ultrasonic multi-element array transducer, the probe being fitted on the poly-articulated robot to make an ultrasound test in the space between two adjacent elements of the single-piece assembly, and an electronic signal processing device, for processing signals output by the ultrasonic multi-element array transducer in order to test the welds.

BRIEF DESCRIPTION OF THE DRAWINGS

This invention will be better understood after reading the description of example embodiments given below purely for informative purposes and in no way limitative with reference to the appended drawings in which.

DETAILED PRESENTATION OF PARTICULAR EMBODIMENTS

The following description is applicable to a blisk for a turbomachine in which the blades are welded to the disk part forming the hub. However, this application is not limitative.

Figure 1:
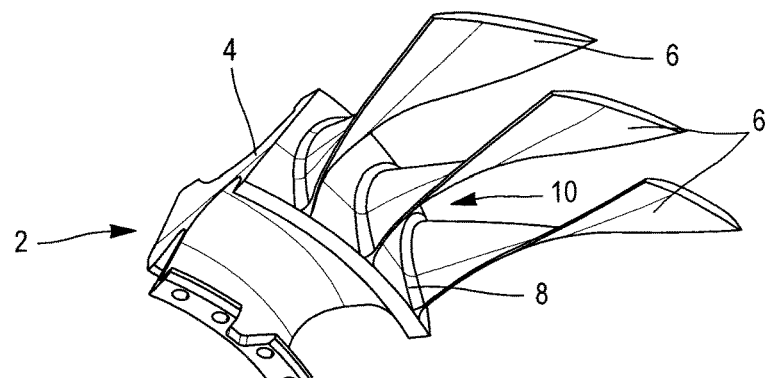
FIG. 1 is a diagrammatic and partial schematic view of a blisk for which it is required to test the welds of blades onto the disk part, FIGS. 2A and 2B diagrammatically show an example of the device according to the invention, FIG. 2C diagrammatically shows an ultrasonic multi-element array transducer with a checkerboard layout, FIG. 2D diagrammatically shows firstly the principle of a test made by working in full-skip and secondly the principle of a test made working in half-skip, FIG. 3 diagrammatically shows tests of a blade in half-skip and in full-skip, FIGS. 4A and 4B diagrammatically show planes inspected by sectorial scanning, FIGS. 5A and 5B diagrammatically show a bevelled probe used preferentially for this invention, and FIG. 5C diagrammatically shows a test made using this probe.

FIG. 1 shows a diagrammatic and partial perspective view of a blisk 2 comprising a disk 4 forming a hub, and blades 6. These blades are welded to the disk 4, for example by linear friction.

Figure 2A:
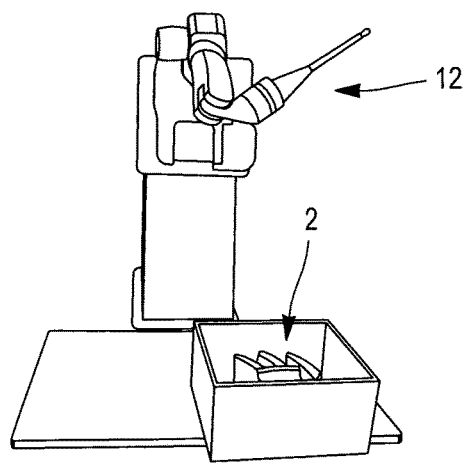
Figure 2B:
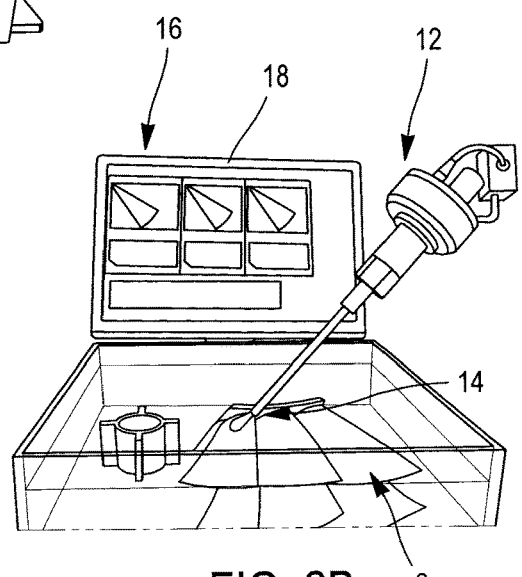

According to the invention, an ultrasound test is made of the welds such as weld 8, also called "welded joint". This test is made in the inter-blade space such as the space 10, between two adjacent blades, using a device comprising a poly-articulated robot 12 (FIG. 2A). This robot is capable of performing three dimensional trajectories. It is fitted with an ultrasonic multi-element transducer, preferably an ultrasonic multi-element array transducer 14 (FIG. 2B).

An "ultrasonic multi-element transducer" refers to a transducer that is composed of a plurality of individual elements, each of which may be controlled independently of the others. Ultrasonic multi-element array transducers, also called "ultrasonic array transducer", have an active part that is divided into different two-dimensional elements.

Figure 2C:
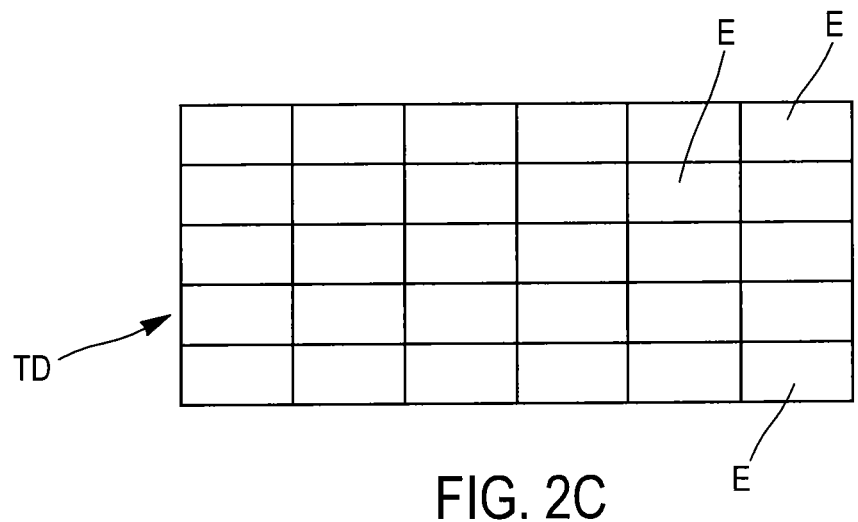

A TD checkerboard type ultrasonic array transducer (FIG. 2C), with multiple elements E, is preferred for testing welds of blades to the disk part of a blisk: such a configuration can be used to control the ultrasound beam in three dimensions.

The testing device also comprises an electronic device 16 to appropriately process the signals output by the transducer 14 and to provide test results. The device 16 is provided with simulation tools (not shown) and a result display device 18.

Figure 2D:
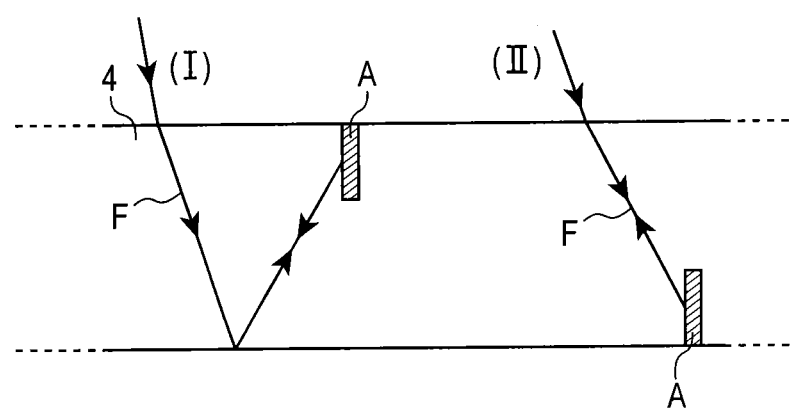

The example shown is a transverse ultrasound wave test. This test is made working firstly in full-skip and also in half-skip. This is diagrammatically shown in FIG. 2D in which the disk 4 can be seen with an ultrasound beam F emitted by a transducer not shown, and a defect or anomaly A. In this FIG. 2D, case I corresponds to work in full-skip and case II corresponds to work in half-skip.

Figure 3:
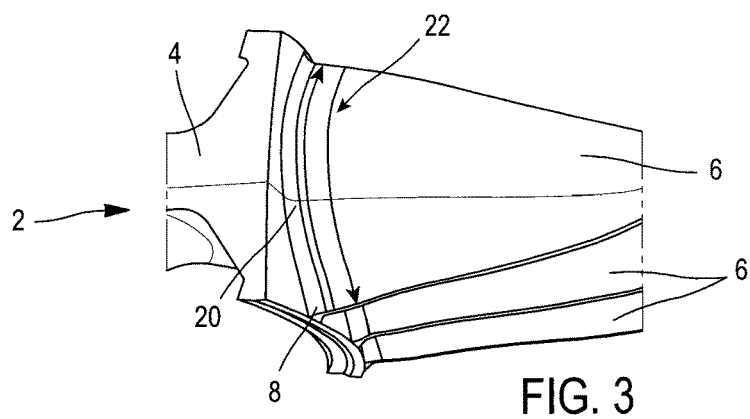

It is thus possible to detect surface and internal anomalies with an ultrasound beam generated from a single side of the disk 4. This requires two test passes (FIG. 3) and can save cycle time and make it easier to program trajectories.

The first pass 20 consists of a half-skip test of the welded joint 8, which is why there is a single skip of the ultrasound beam on the bottom of the corresponding blade 6.

The second pass 22 consists of a full-skip test of the welded joint 8, which is why there is a skip of the ultrasound beam on the bottom of the blade 6 and then on its surface.

In order to compensate for geometry effects, the poly-articulated robot 12, also called "robotised arm", is used to follow the complex profile along the blade 6, at two constant and different distances from the welded joint plane 8, to limit the number of trajectories in the reduced space formed by the inter-blade space 10. This robotised profile following is usually necessary but it cannot compensate for the effect of deviations of the ultrasound beam in three dimensions due to interaction between this ultrasound beam and the surface of the welded joint 8 (according to Snell-Descartes's laws).

Figure 4A:
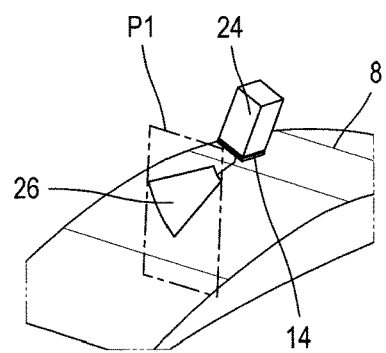
Figure 4B:
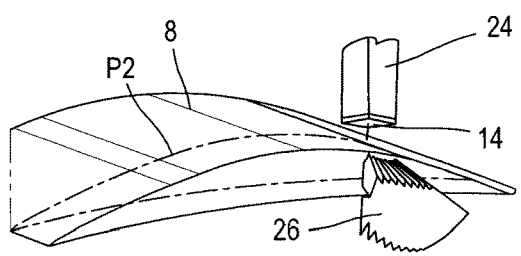

Thus, this profile following is preferably complemented by sectorial electronic scanning (done by the ultrasound beam) in two test planes shown in FIGS. 4A and 4B. This also contributes to treating the thickness of the zone to be tested, and the thickness varies depending on the profile of the blade 6.

Remember that electronic scanning consists of moving the ultrasound beam in space by sequentially activating each element of the ultrasonic multi-element array transducer. This type of scanning can electronically replace a mechanical scanning axis. Electronic scanning is very suitable for testing welds.

The first test plane P1 can be seen in FIG. 4A and the second test plane P2 can be seen in FIG. 4B. These planes P1 and P2 are not parallel and are preferably approximately orthogonal.

The combination of multi-plane electronic scans makes it possible to compensate for the deviation of the ultrasound beam. When a matrix probe is being used (ultrasound probe fitted with an ultrasonic multi-element array transducer), it is preferable to use two approximately orthogonal planes in order to globally cover the volume, characterised by a variation in the thickness and the profile to be followed.

The welded joints such as the welded joint 8 are very diagrammatically shown In FIGS. 4A and 4B.

In these FIGS. 4A and 4B, a probe 24 is also diagrammatically shown in which the ultrasonic multi-element array transducer 14 is included with one or several ultrasound beams 26 emitted in sequence by the transducer 14. The probe 24 is fitted on the free end of the poly-articulated robot 12 (FIG. 2B), so that it can perform three-dimensional trajectories along the profile of the blade for which the weld is to be tested.

The inter-blade space 10 is small (typically 35 mm maximum) and has concave and then convex geometries. This is why a chamfered probe is used 24, for which the design and the geometry are adapted to the small size in question. More precisely, a bevelled probe is advantageous because it can easily be inserted between two adjacent radial elements, as close as possible to the hub (and facing the tested welded joint) and is adapted to the space between the elements. In the example described, the bevelled probe 24 is as shown in FIGS. 5A and 5B.

Figure 5A:
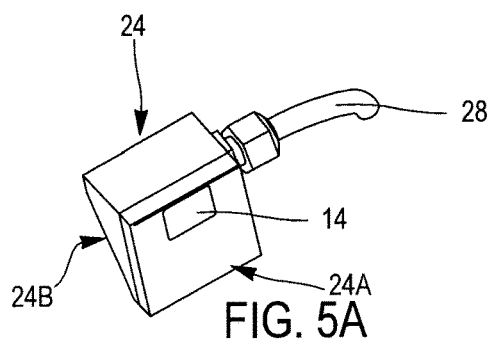
Figure 5B:
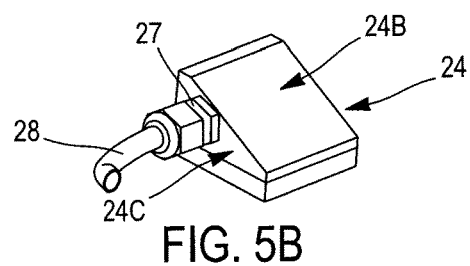

These FIGS. 5A and 5B are diagrammatic perspective views of the bevelled probe 24. FIG. 5A is a bottom view and the transducer 14 can be seen in it. FIG. 5B is a top view. The probe 24 is generally wedge-shaped, including a coupling face 24A comprising the transducer 14 and another face 24B opposite the coupling face 24A that makes an acute angle of about 30° with the coupling face. A side face 24C of the probe 24 comprises a connection element 27. This connection element is connected to a cable 28 that transmits signals output by the transducer 14 to the electronic processing device 16 (FIG. 2B) through the connection element 27.

Figure 5C:
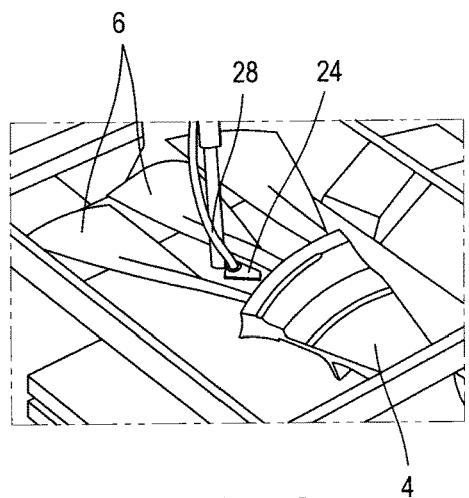

FIG. 5C diagrammatically shows a test of one of the welds using this probe.

In the example described, the following test protocol is used:

Phase 1: Configuration Definition
    Enter the characteristics of the transducer into the acquisition software used (particularly the shape, frequency, dimensions of ultrasound emitter-receiver elements included in the transducer, number of these elements, etc.)
    Enter the characteristics of the blades and the blisk (particularly CAD (Computer Aided Design) data and materials)
    Enter the test configuration (particularly angulation of the transducer and the water head).
    Calculate delay laws to control the transducer.

Phase 2: Settings
    Calibration on one or several reference parts (particularly an artificial reflector).
    Settings of "gates", in other words intervals of numeric values of test parameters (particularly distance and amplitude)
    Definition of the test sequence (particularly trajectories, turntable, chaining of passes)

Phase 3: Acquisitions and Analysis

The small inter-blade space led to the design of a bevelled probe. However in one variant not shown, a tool holder with a curved shape adapted to the inter-blade space is designed to hold this probe at the free end of the poly-articulated robot 12 (FIG. 2B). This tool holder provides additional aid in passing and displacement of the probe in the inter-blade space, considering the small space available for the probe.

Note also that poly-articulated robot trajectories were programmed by learning. Man-machine interaction makes use of a digital file of the blisk, in other words of the disk part and welded blades. Note also that a link between the electronic control software associated with the multi-element transducer and the theoretical trajectory defined in the digital file, enables a more precise trajectory.

In the example described above, it was possible to test the welds or welded joints taking account of the complex geometry of the welds by compensation of deviations of the ultrasound beam by electronic scanning in two directions.

Therefore the invention described above is particularly applicable to testing welds of a blisk for a turbomachine. However, the weld testing method according to the invention and the test device used in the invention can be applied to other fields than the field of blisks for turbomachines.

The invention claimed is:

1. A method for testing element welds on a body, the body and the elements that are welded to the body forming a single-piece assembly, the method comprising: equipping a free end of a poly-articulated robot with an ultrasound probe, fitted with an ultrasonic multi-element array transducer, the elements of said transducer being arranged in a checkerboard layout; inserting the ultrasound probe into a space between two adjacent elements of the single-piece assembly, facing a welded joint, corresponding to one of the two elements for which a weld is to be tested; moving the ultrasound probe along three-dimensional trajectories along a profile of the element for which the weld is to be tested; performing at least two sectorial electronic scannings in at least two non-parallel testing planes which are approximately orthogonal for each of a plurality of acquisition points along each of the three-dimensional trajectories; processing the resulting sectorial electronic scans to compensate for an effect of deviations of an ultrasound beam output by the ultrasonic multi-element array transducer due to an interaction of the ultrasonic multi-element array transducer with a surface of the welds between the body and the elements; and further processing ultrasound signals output by the transducer in order to test the welds.

2. The method according to claim 1, wherein the test is a test by transverse ultrasound waves.

3. The method according to claim 2, wherein testing is made by working in full-skip and in half-skip.

4. The method according to claim 3, further comprising testing the welded joint of each element by performing a first pass to test the welded joint in half-skip and a second pass to test the welded joint in full-skip.

5. The method according to claim 4, further comprising using the poly-articulated robot to follow the profile along each element, at a first constant distance from a corresponding joint plane and at a second constant distance from the corresponding joint plane different from the first distance.

6. The method according to claim 1, wherein the ultrasound probe is a beveled probe, adapted to the space between the two adjacent elements of the single-piece assembly.

7. The method according to claim 1, further comprising:
using a data acquisition software,
entering characteristics of the transducer, characteristics of the single-piece assembly, and a test configuration in the data acquisition software,
calculating delay laws for the transducer,
making a calibration on a reference part,
adjusting intervals of numeric values of test parameters,
defining a test sequence, and
acquiring signals output by the transducer and analyzing the signals to test the welds.

8. The method according to claim 1, wherein the elements are composed of blades, and the body includes a disk part of an assembly forming a turbomachine blisk, the test being a test of the welds of the blades on the disk part of the blisk.

9. The method according to claim 1, wherein the sectorial electronic scanning in at least two approximately orthogonal testing planes is performed in a single pass for each of the plurality of acquisition points.

10. A device for testing welds of elements on a body, the body and the elements welded to the body forming a single-piece assembly, the device comprising: a poly-articulated robot, capable of making three-dimensional trajectories;
an ultrasound probe, fitted with an ultrasonic multi-element array transducer, the elements of said transducer being arranged in a checkerboard layout, the probe being fitted on the poly-articulated robot to make an ultrasound test in a space between two adjacent elements of the single-piece assembly, wherein the ultrasound probe is arranged for performing at least two sectorial electronic scannings in at least two non-parallel testing planes which are approximately orthogonal for each of a plurality of acquisition points along a three-dimensional trajectory; and an electronic signal processing device configured to process the sectorial electronic scans to compensate for an effect of deviations of an ultrasound beam output by the ultrasonic multi-element array transducer due to an interaction of the ultrasonic multi-element array transducer with a surface of the welds between the body and the elements and further configured to process signals output by the ultrasonic multi-element array transducer in order to test the welds.

11. The device according to claim 10, wherein the polyarticulated robot and the ultrasound probe are arranged for performing the sectorial electronic scanning in at least two approximately orthogonal testing planes in a single pass for each of the plurality of acquisition points.

* * * * *